United States Patent
Nelson

(10) Patent No.: US 7,298,820 B2
(45) Date of Patent: Nov. 20, 2007

(54) PORTAL IMAGING USING MODULATED TREATMENT BEAM

(75) Inventor: Ian A. Nelson, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 70 days.

(21) Appl. No.: 11/394,727

(22) Filed: Mar. 31, 2006

(65) Prior Publication Data

US 2007/0237304 A1  Oct. 11, 2007

(51) Int. Cl.
*G01N 23/04* (2006.01)
*A61N 5/10* (2006.01)

(52) U.S. Cl. .................... 378/65; 378/62; 378/98.9; 378/160; 378/207

(58) Field of Classification Search .............. 378/62, 378/65, 98.9, 160, 207
See application file for complete search history.

(56) References Cited

U.S. PATENT DOCUMENTS

| | | | |
|---|---|---|---|
| 4,541,106 A * | 9/1985 | Belanger et al. ......... 378/98.11 |
| 5,233,990 A * | 8/1993 | Barnea ....................... 600/427 |
| 6,208,712 B1 | 3/2001 | Hernandez-Guerra |
| 6,735,273 B2 * | 5/2004 | Flohr et al. ..................... 378/5 |
| 6,810,107 B2 * | 10/2004 | Steinberg ..................... 378/65 |
| 6,836,570 B2 * | 12/2004 | Young et al. ............... 382/274 |
| 6,937,693 B2 * | 8/2005 | Svatos ......................... 378/65 |
| 7,021,118 B2 * | 4/2006 | Sundermann et al. ........ 73/1.79 |
| 2004/0022363 A1 | 2/2004 | Ghelmansarai |
| 2004/0068182 A1 | 4/2004 | Misra |
| 2005/0152495 A1 | 7/2005 | Hesse |
| 2006/0291621 A1* | 12/2006 | Yan et al. ..................... 378/65 |
| 2007/0018117 A1* | 1/2007 | Calderon et al. ......... 250/492.1 |

\* cited by examiner

*Primary Examiner*—Courtney Thomas
*Assistant Examiner*—Thomas R. Artman
(74) *Attorney, Agent, or Firm*—Quarles & Brady LLP

(57) ABSTRACT

A radiation therapy system produces a treatment beam that is detected by an electronic portal imaging device (EPID) after it passes through the subject being treated. A chopper wheel modulates low energy components of the beam while leaving the higher energy components substantially unmodulated. Modulated components in the image signals produced by the EPID are detected and used to produce portal images.

11 Claims, 4 Drawing Sheets

PORTAL IMAGING USING MODULATED TREATMENT BEAM

STATEMENT REGARDING FEDERALLY SPONSORED RESEARCH

This invention was made with government support under Grant No. 5T32 CA09 206-27 awarded by the National Institute of Health. The United States Government has certain rights in this invention.

BACKGROUND OF THE INVENTION

This invention relates to radiation therapy equipment for the treatment of tumors or the like and specifically to an improved method of characterizing the radiation beam of such systems and confirming the dose received by the patient using a portal image of radiation exiting the patient.

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}$Co, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam thus change as the gantry rotates around the subject, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, some of which use multiple sliding shutters which, piecewise, may generate a radio-opaque mask of arbitrary outline.

The radiation beam may also be controlled by insertion of wedges or blocks into the beam to reduce the intensity or fluence of the beam by means of attenuation in some areas. U.S. Pat. No. 5,317,616 issued May 31, 1994, incorporated by reference and assigned to the same assignee as the present invention, describes a shutter system that provides an alternative to wedges for reducing fluence or intensity portions of the radiation beam by temporally changing the radiation beam with collimator leaves.

In order to confirm the positioning of the collimation blades and blocks used in a particular radiation therapy session, a "portal image" may be obtained in which treatment radiation exiting from the patient is recorded on x-ray film or the like. A visual examination of this image provides a radiograph that gives a gross indication that the "geometry" of the radiation beam is correct.

Electronic portal imaging devices (EPIDs) are becoming standard features on medical linear accelerators for radiotherapy. These devices enable one to form an anatomical x-ray image of a patient using the high energy treatment beam (average photon energy approximately 2 MeV). Image quality, however, is significantly worse than that routinely achieved in low energy diagnostic x-ray imaging devices for two main reasons, both related to energies of the photons in the beam.

First, most of the contrast in a low energy diagnostic x-ray image comes from the photoelectric effect. Photoelectric absorption of the x-ray photons is proportional to the cube of the atomic number of the absorber. This is why bone (Z=12.5) and soft tissue (Z=7.4) are easily differentiated in a diagnostic x-ray image [$(12.5/7.4)^3=5$]. Photons with energies above approximately 50 keV interact primarily via Compton scattering, which is independent of atomic number. The rate of Compton interaction of high energy x-rays is simply proportional to electron density. Bone (approx. 5E29 electrons/cc) and soft tissue (approx. 3E29 electrons/cc) are therefore discernable in high energy x-ray images, but contrast is much poorer.

The second problem with high energy x-ray imaging is the nature of Compton interactions versus photoelectric interactions. In a low energy photon interacting via the photoelectric effect the photon is completely absorbed by an electron and does not reach the detector. High energy photons undergoing Compton interactions are not absorbed, however, but instead, they are scattered through some angle. These scattered photons reach the detector and contribute to an image 'fog' that further obscures the (already marginal) image detail.

The treatment beams from medical linear accelerators are not monoenergetic, but instead contain an entire spectrum of photon energies ranging from zero up to the nominal energy of the beam (e.g. 6 MeV). Therefore there is, in principle, a good quality image formed by low energy photons in the beam, but it is entirely obscured by the low contrast and scatter contributed by the much more prevalent high energy photons.

SUMMARY OF THE INVENTION

The present invention is an improvement to radiation therapy systems which enables higher quality portal images to be produced from the treatment beam and during the treatment process. The invention includes a chopper which is constructed to modulate the intensity of the low energy components of the treatment beam while leaving the higher energy components therein substantially unmodulated. A detector receives the treatment beam after it passes through the subject being treated and produces corresponding signals. The modulated signal components therein are separated and used to produce images during the treatment process.

An object of the invention is to remove from the portal images the high energy components of the image signal and the components related to Compton scatter. This is achieved by modulating the desired low energy components of the treatment beam and retaining the resulting modulated signal components in the video signals to produce the displayed images.

DETAILED DESCRIPTION OF THE PREFERRED EMBODIMENT

Figure 1:
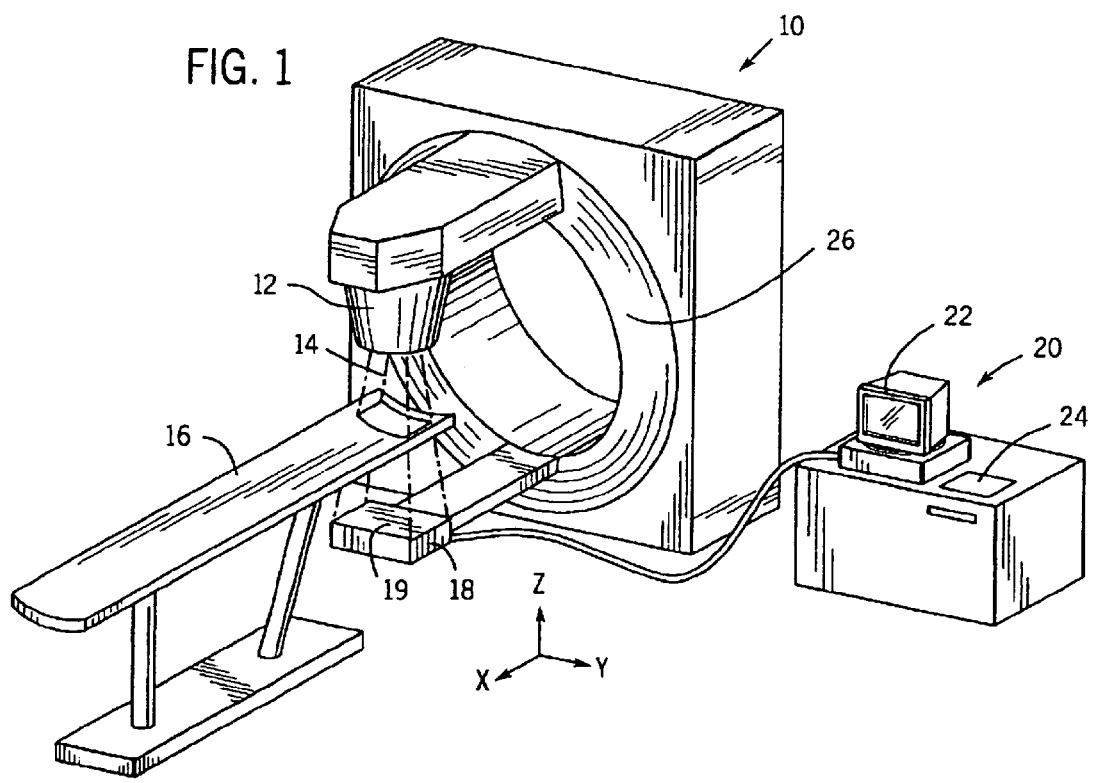
FIG. 1 is a pictorial view of a radiation therapy system that employs the preferred embodiment of the invention.
Figure 2:
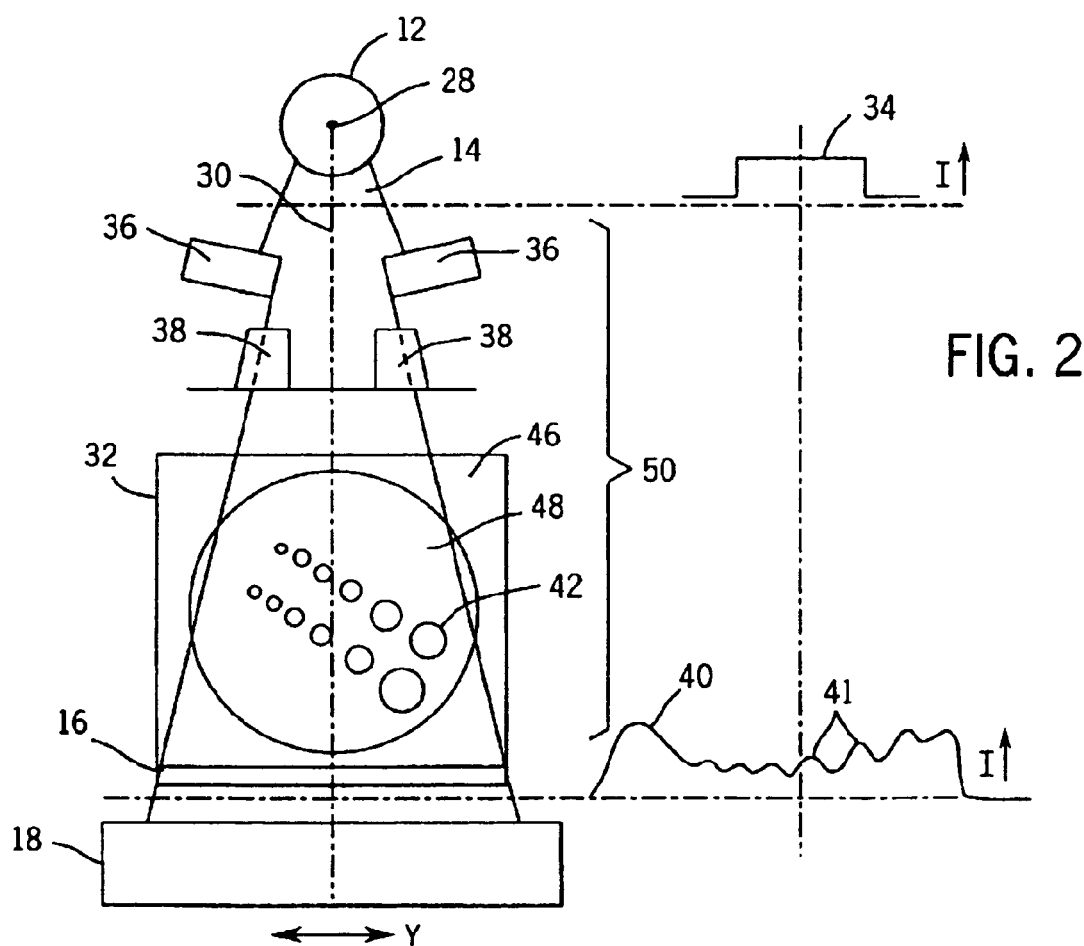
FIG. 2 is a schematic representation of the x-ray beam path in the system of FIG. 1.

Referring to FIG. 1, a radiation therapy system 10, suitable for use in the present invention, includes a radiation source 12 producing a radiation beam 14 directed across a patient support table 16 that may hold a patient (not shown) or a calibration phantom 32 (shown in FIG. 2). The radiation beam 14 may be a megavoltage x-ray beam (e.g., 6-10 megavolts) or other photon source suitable for radiation therapy. The radiation beam 14, as shown, is collimated to a fan shape; however, the invention is equally applicable to "cone beams" of radiation.

After passing through the patient support table 16 and either the patient or a calibration phantom 32, the beam 14 is received by an electronic portal imaging device (EPID) 18 having a detector surface 19 corresponding to the cross-sectional area of the beam 14. EPID 18 produces electronic signals providing measurements of the dose of the radiation received at regularly spaced positions, or pixel locations over the detector surface 19. Thus, the portal imaging device 18 generally provides the data of a projection image through the patient or phantom 32 along an axis of the radiation beam 14 at an arbitrary angle.

The EPID 18 is a flat panel Silicon, or Si detector. It includes a detector surface 19 formed of a phosphor layer that emits light when struck by x-rays. A two-dimensional array of Si photodiodes are disposed beneath the phosphor layer and each is connected to a thin film transistor. Each photodiode and thin film transistor form a pixel in the EPID 18 that accumulates charge in proportion to the x-rays striking the phosphor layer above it. The accumulated charges are read out of the detector elements one column at a time, amplified and converted to corresponding 16-bit digital values. As will be described further below, each column of digital pixel values in the EPID 18 are read out in sequence by a frame grabber and used to produce a portal image of the subject being treated. It should be apparent that other detector technologies such as CCD and MOSFET may be used in this application.

The EPID 18 and radiation source 12 are mounted in opposition about the patient support table 16 on a rotating gantry 26. The patient support table 16 may be tipped so that, together with rotation of the gantry 26, the beam 14 may be directed at the patient or phantom 32 from a variety of angles as is understood in the art.

The signals from the EPID 18 are transmitted to a computer 20 where it is converted into a matrix of digital values; the values indicate the dose of radiation at each point of the detector surface 19. Computer 20 includes a display terminal 22 for displaying images and text and a keyboard 24 for user entry of data.

Referring also to FIG. 2, the beam 14 of radiation diverges from a focal point 28 within the radiation source 12 and is directed generally along a radiation axis 30 toward a phantom 32 (or patient not shown in FIG. 2) resting on top of the support table 16. Ideally, the beam 14, as emitted from the radiation source 12 with coarse collimation (not shown) has an essentially uniform beam fluence profile 34 referring to its intensity throughout its cross-sectional area, measured in a plane perpendicular to the axis 30.

In practice, the beam fluence profile 34 will deviate from perfect uniformity, even after the interposition of a flattening filter and other adjustment of the radiation source 12 known to those of ordinary skill in the art. For this reason, as will be described below, it is typical to make measurements of phantoms 32 in the beam 14 to account for any non-uniformity.

Beam 14 is next collimated by collimator blocks 36 which determine the outline of the beam that will ultimately be received by the patient or phantom 32. Collimator blocks 36 are radio-opaque and may be used, for example, to match the beam width to the outline of a tumor.

The collimated radiation beam 14 is next received by wedges 38 which serve to reduce the intensity of certain rays within the radiation beam 14 as is well understood in the art. The wedges 38 are placed so as to better control the desired dose to particular areas of the patient during radiation treatment and to compensate for varying thicknesses of the intervening tissue of the patient. As shown in FIG. 2, wedges 38 decrease the intensity of the edge rays of the beam 14 that pass through portions of the phantom 32 where the phantom is substantially thinner as might be desired to reduce dose to these areas in a human patient.

After the radiation of the beam 14 exits the phantom 32, it may be recorded as a portal image 40, the portal image 40 being the measure of the dose of the beam 14 throughout its cross-sectional area in a plane perpendicular to the axis 30 after exiting the patient or phantom 32.

Figure 3:
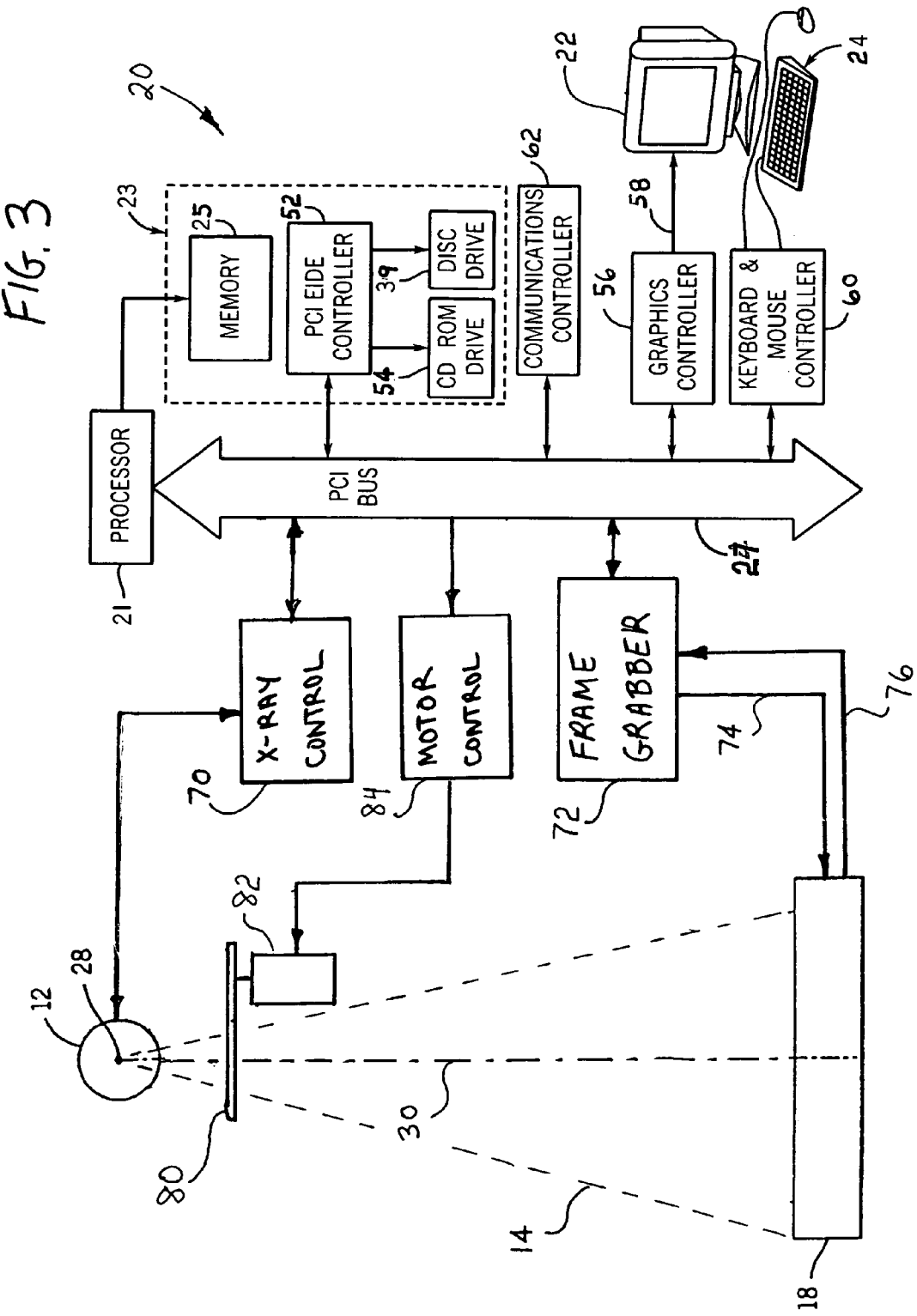
FIG. 3 is a schematic diagram of the workstation that forms part of the therapy system of FIG. 1.

Referring particularly to FIG. 3, the computer workstation 20 includes a processor 21 which executes program instructions stored in a memory 25 that forms part of a storage system 23. The processor 21 is a commercially available device designed to operate with one of the Microsoft Corporation Windows operating systems. It includes internal memory and I/O control to facilitate system integration and integral memory management circuitry for handing all external memory 25. The processor 21 also includes a PCI bus driver which provides a direct interface with a 32-bit PCI bus 27.

The PCI bus 27 is an industry standard bus that transfers 32-bits of data between the processor 21 and a number of peripheral controller cards. These include a PCI EIDE controller 52 which provides a high-speed transfer of data to and from a CD ROM drive 54 and a disc drive 39. A graphics controller 56 couples the PCI bus 27 to the CRT monitor 22 through a standard VGA connection 58, and a keyboard and mouse controller 60 receives data that is manually input through a keyboard and mouse 24.

The PCI bus 27 also connects to a communications controller 62. The controller 62 connects to an intranet that links the workstation 20 to other institution systems such as imaging systems, PAC systems and treatment systems.

The PCI bus 27 is also coupled to the radiation source 12 through an x-ray control 70. The x-ray control 70 enables the source 12 to be controlled by commands received from the PCI bus 27. The source 12 is thus under the control of software executed by the processor 21 during a treatment procedure.

The read out of the charge accumulation in the EPID 18 is also under software control. A frame grabber 72 connects to the PCI bus 21 and issues read out commands to the EPID 18 over control line 74. Each column of the two-dimensional array of pixel charge data is read out over bus 76 and stored in the frame grabber 72. The two-dimensional charge image that results when all the columns have been read are then transferred to memory 25 for further processing as will be described in more detail below.

Figure 4:
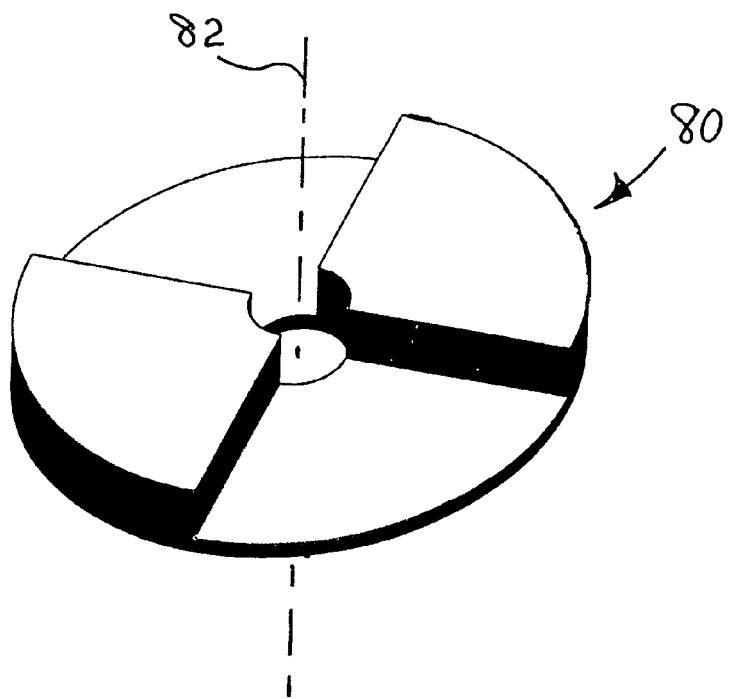
FIG. 4 is a perspective view of a chopper wheel that forms part of the system of FIG. 3.

An important aspect of the present invention is the modulation of the x-ray beam 14 produced by the source 12. Referring particularly to FIGS. 3 and 4, this is accomplished by mounting a chopper wheel 80 adjacent the source 12 and positioning it to intercept the x-ray beam. The chopper wheel 80 is rotated about an axis 82 that is parallel to the x-ray beam axis 30 and alternate thick and thin segments of the wheel 80 are rotated into the beam 14 to alternately block and pass low energy photons.

The chopper wheel 80 is rotated by a motor 82. The motor 82 is in turn driven by a motor control 84 that interfaces to the PCI bus 27. The rotation of the chopper wheel 80 and its alignment (attenuation or no attenuation) in the beam 14 is, therefore, under software control.

The chopper wheel 80 is constructed to alternately block and pass the lower energy x-rays while imposing minimal attenuation of the high energy x-rays.

The concept is to modulate the low energy x-rays that will be used to produce the portal image while having a minimum impact on the remainder of the treatment x-rays. There are many materials that will accomplish this, but in the preferred embodiment a 0.75 mm thick aluminum foil is used for the beam blocking wheel segments and a 0.20 mm thick molybdenum foil is used for the beam passing wheel segments. This choice enables the thickness to be minimized with two materials having very similar x-ray absorption cross-sections (z). The high energy material (molybdenum) determines the high energy cutoff of the 'energy window' selected for modulation by the chopper wheel 80. Molybdenum is chosen because its Z (42) is fairly high, it is inexpensive, stable, and readily available. Higher Z materials (lead, tungsten, etc.) are less ideal because they have x-ray absorption lines within the desirable 'energy window' which serve to reduce the amount of modulation that can be achieved. After the high Z material is chosen, the thickness is chosen such that the majority of photons with energies within the desirable low energy window are blocked while the majority of photons with energies above the desirable window are passed (preferably greater than 99% transmission at 2 MeV). As a result, the low energy photons will be heavily modulated while the high energy photons are modulated only slightly. The slight modulation that does affect the high energy photons can be reduced by the addition of the low Z material. A thickness of low Z material is selected to provide very nearly the same transmission of high energy photons (>99%) as the chosen high Z material—this is the region where (Z-independent) Compton interactions predominate—while simultaneously providing high transmission of the photons with energies within the lower energy window—the region where (Z-dependent) photoelectric interactions predominate. Because the transmission curves for different materials are shaped slightly differently, it is desirable to keep the thickness to a minimum in order to make the cancellation of the modulation on the high energy photons more complete across a wide range of energies.

With the preferred chopper wheel construction the high energy x-ray photons are not significantly attenuated by either the beam pass or the beam block segments. In the range of 1 MeV to 6 MeV an attenuation of <1% is expected from the blocking and the passing chopper wheel segments. On the other hand, x-rays in the lower energy range around 50 keV are attenuated 75% by the beam blocking segment and only 7% by the beam passing chopper wheel segments. Little modulation of the high energy x-rays results and the signals acquired by the EPID 18 which are attributable to high energy x-rays are not significantly affected. On the other hand, the low energy x-rays that are suitable for diagnostic imaging are modulated and the amplitude of the signals acquired by the EPID 18 which are attributable to low energy x-ray photons vary over time in a pattern that corresponds to the modulation frequency. In the preferred embodiment the EPID 18 produces 30 images per second and the chopper wheel 80 is rotated at a speed which modulates the low energy x-rays at 15 Hz. The x-ray beam 14 is thus sampled by the EPID 18 at twice the frequency of the modulation.

The image frames that are received through the frame grabber 72 at a rate of 30 per second are stored in memory 25 and processed to separate all the components therein which are modulated at 15 Hz. Thus, the unmodulated high energy x-ray beam components and the components produced by compton scatter are removed. The separated components produce a much higher quality portal image and may be stored for later use, sent to another cite through the communications controller 62 or displayed on screen 22 in near real time as the treatment procedure is carried out.

Figure 5:
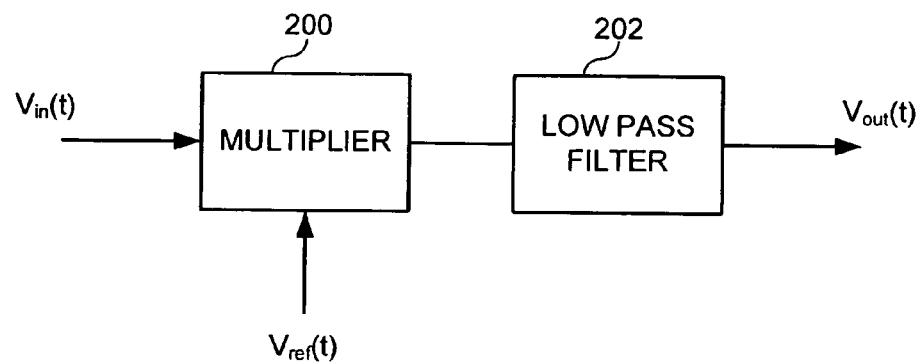
FIG. 5 is a block diagram of an alternative demodulator circuit used to separate the modulated signal components.

The separating of the modulated 15 Hz components can be done in many different ways. For example, a "lock-in circuit" may be constructed as part of the EPID 18 or the frame grabber 72 to demodulate the sequence of image frames as they are received. Such a demodulator is shown in FIG. 5, where the input signal $V_{in}(t)$ may be an analog signal produced by one pixel in the EPID 18 before it is digitized therein, or it may be the stream of digitized signals from the EPID pixel. In either case, the input signal $V_{in}(t)$ is multiplied at 200 by a reference signal $V_{ref}(t)$, which is the beam modulation frequency, and the result is low pass filtered at 202. The analog version of this demodulator is constructed as part of the EPID 18, whereas the digital version is constructed as part of the frame grabber 72. The reference signal $V_{ref}(t)$ may be produced by the motor control 84, but preferably is produced by a sensor (not shown) that detects the orientation of the chopper wheel 80.

In the preferred embodiment this separating function is accomplished under software control using a boxcar averaging with baseline subtraction. This is done by subtracting the signal magnitude at corresponding pixels in successive pairs of acquired image frames. That is, the digitized detector signals at corresponding pixels in successive image frames are subtracted from one another to produce a difference image frame. The resulting difference image frames are produced at a rate of 15 image frames per second and these depict the intensity of the detected low energy x-rays. The ill affects caused by the detected high energy x-rays and detected Compton scatter are not seen.

During a treatment procedure the x-ray source 12 is turned on and the gantry 26 is rotated to treat the tumor in a patient placed on the table 16. Simultaneously, low energy image frames are produced in near real time and displayed on the screen 22 at 15 frames per second. These images enable the physician to more accurately monitor the treatment process.

The invention claimed is:

1. A system for producing a portal image from a treatment beam produced by a radiation therapy system, the combination comprising:
   a chopper mounted on the radiation therapy system and positioned to intercept the treatment beam, the chopper being operable to modulate the intensity of low energy components in the treatment beam;
   a detector mounted on the radiation therapy system and positioned to receive the treatment beam after it passes through the chopper and a subject being treated, the detector producing signals indicative of the treatment beam components passing through the subject;
   means for separating the modulated signal components from the detected signal; and
   means for producing an image with the separated signal components.

2. The system as recited in claim 1 in which the chopper includes two segments that are alternately moved into the treatment beam, wherein one of the segments is made of a material that absorbs a substantial portion of the low energy components in the treatment beam and an insubstantial portion of the higher energy components in the treatment beam.

3. The system as recited in claim 2 in which the chopper is a rotatable wheel.

4. The system as recited in claim 1 in which the chopper is positioned to intercept the treatment beam before it passes through the subject.

5. The system as recited in claim 1 in which the detector produces said signals in the form of a series of image frames and each signal indicates the intensity of the detected treatment beam at one pixel location in the image frames.

6. The system as recited in claim 5 in which each image frame is a digitized representation of the signal values at each pixel location at a point in time; and
   the means for separating the modulated signal components includes a programmed processor that receives the image frames and processes them.

7. The system as recited in claim 6 in which the processing includes producing difference image frames by subtracting successive pairs of received image frames.

8. The system as recited in claim 7 in which the rate at which the detector produces image frames is twice the rate at which the lower energy components in the treatment beam are modulated.

9. The system as recited in claim 1 in which the means for separating includes a lock-in circuit.

10. The system as recited in claim 1 in which the means for separating includes a demodulator circuit.

11. The system as recited in claim 10 in which the demodulator circuit includes a multiplier circuit and a low pass filter circuit.

* * * * *